Figure 1:
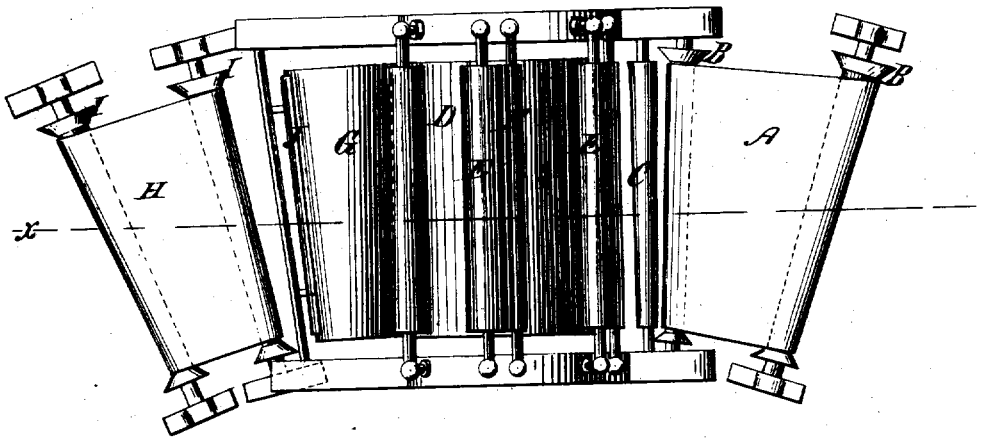

H. J. & W. D. DAVIES.

Carding-Engine for Making Bats for Felted Fabrics.

No. 6,432. Reissued May 18, 1875.

Witnesses:
Michael Ryan
Fred Haynes

H. J. Davies
W. D. Davies
by their Attorneys
Brown & Allen

THE GRAPHIC CO PHOTO-LITH. 39 & 41 PARK PLACE, N.Y.

UNITED STATES PATENT OFFICE.

HENRY J. DAVIES AND WALTER D. DAVIES, OF BROOKLYN, NEW YORK, ASSIGNORS TO BENNETT & SMITH.

IMPROVEMENT IN CARDING-ENGINES FOR MAKING BATS FOR FELTED FABRICS.

Specification forming part of Letters Patent No. 155,503, dated September 29, 1874; reissue No. 6,432, dated May 18, 1875; application filed April 12, 1875.

*To all whom it may concern:*

Be it known that we, HENRY J. DAVIES and WALTER D. DAVIES, both of the city of Brooklyn, in the county of Kings and State of New York, have invented certain new and useful Improvements in Carding-Engines for Making Bats for Felted Fabrics; and we do hereby declare that the following is a full, clear, and exact description of the same, reference being had to the accompanying drawing forming part of this specification.

The object of this invention is the manufacture of felted fabrics in a sheet or web of curved form, its edges presenting concentric arcs of different radiuses, such fabrics being especially suitable for making skirts by forming the web of a width equal to the desired length of the skirt, and then cutting said web transversely into a suitable length for the circumference of the skirt, which will be of larger measurement at its bottom than its top, and afterward uniting the ends of such web by a single seam to produce the skirt.

The most important feature of the invention consists in a conical doffer, by which, owing to its circumference being greater at one end than the other, the bat is made of greater length at one edge than the other, and, when taken off and laid out flat, is made to present the curved form hereinabove mentioned.

The invention also consists in a feed-apron, having its length varying from one edge to the other, and arranged on conical rollers, the axes of which converge toward a common center. The larger ends of these rollers and longer side of the feed-apron are arranged on the same side of the carding-engine as the larger end of the doffer. By this construction and arrangement of this apron and its rollers the feeding of a larger quantity of stock toward that end of the main carding-cylinder against which the larger end of the doffer works is facilitated.

The invention further consists in a delivery-apron having its length increased toward that side of the machine at which the larger end of the doffer is situated, such increase of length being proportioned to the increased circumference of the doffer.

The invention does not necessitate any change from the usual form of the main carding-cylinder, and the workers and strippers of the carding-engine, and we have therefore represented in the accompanying drawing, which illustrates our invention, a carding-engine, having the main cylinder-workers and strippers of the usual cylindrical form.

Figure 2:
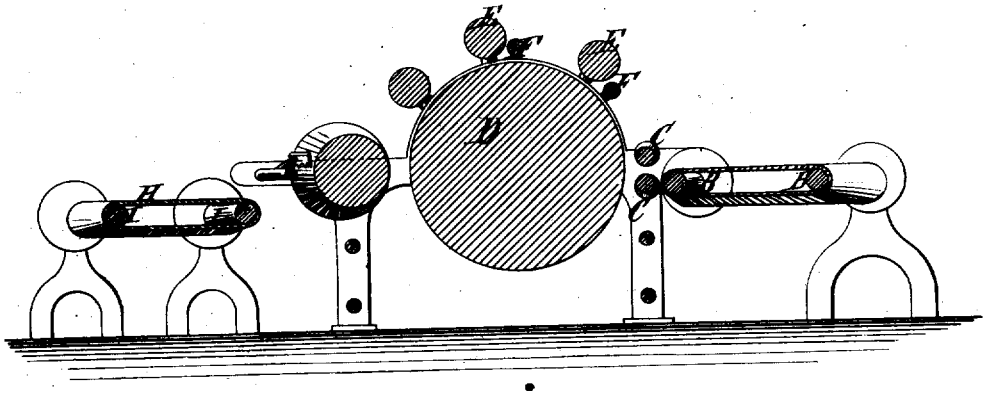

Figure 1 is a plan view of the engine; and Fig. 2, a vertical section of the same on the line *x x*, indicated in Fig. 1.

A is the feeding-apron, onto which the wool or stock is laid to conduct it to the carding-cylinder, said apron being of varying length throughout its width, and traveling around conical rollers B B, the axes of which converge to a common center. C C are similarly tapering feed-rollers arranged at the delivery end of the receiving-apron, and having their inner sides parallel with the carding-cylinder, the same serving to conduct the wool or bat (preferably through the interposition of the usual distributing roller or receiver) to the carding-cylinder D, which has applied in proper relation with it the workers and strippers F E. G is the conical doffer, having its shaft so arranged in its bearings that the portion of its surface nearest the main cylinder is parallel with the adjacent portion of the said cylinder. J is the comb, by which the bat is taken from the doffer. H is the delivery-apron, of varying length throughout its width, that edge which is on the same side of the machine with the larger end of the doffer being of greater length than that on the opposite side, and the increasing length corresponding with the increasing circumference of the doffer. This apron is represented as supported on conical rollers I I, the axes of which and of the doffer converge to a common center.

The process of carding in an engine with these improvements does not differ in any important particular from that in an ordinary carding-engine, except that, owing to the increasing circumference of the doffer from one end to the other, the bat or web produced is of increasing length from one edge to the other, and when laid out flat presents a curved form, its edges being in the form of concentric arcs of different radius. It is to provide for taking up such bat that the delivery-apron is made of varying length throughout its width.

I claim—

1. The doffer G, of conical form, substantially as and for the purpose herein specified.

2. The feeding-apron A, of varying length throughout its width, and its conical rollers B B, in combination with the carding-cylinder D, substantially as specified.

3. The delivery-apron H, of varying length throughout its width, in combination with the conical doffer of a carding-engine, substantially as herein set forth.

HENRY J. DAVIES.
WALTER D. DAVIES.

Witnesses:
BENJAMIN W. HOFFMAN,
FRED. HAYNES.